United States Patent [19]

Bruns et al.

[11] Patent Number: 4,737,322
[45] Date of Patent: Apr. 12, 1988

[54] INTRAOCULAR LENS STRUCTURE WITH POLYIMIDE HAPTIC PORTION AND METHODS FOR FABRICATION

[75] Inventors: Willis J. Bruns, Redlands; Charles M. Kienholz, San Dimas, both of Calif.

[73] Assignee: Staar Surgical Company, Monrovia, Calif.

[21] Appl. No.: 781,232

[22] Filed: Sep. 27, 1985

[51] Int. Cl.⁴ .................... B29D 11/00; A61F 2/16
[52] U.S. Cl. .................... 264/1.7; 264/2.5; 264/221; 264/278; 264/317; 623/6
[58] Field of Search ............ 264/1.1, 1.7, 2.6, 278, 264/2.5, 221, 317; 425/808; 623/6

[56] References Cited

U.S. PATENT DOCUMENTS

| | | | |
|---|---|---|---|
| 4,104,339 | 8/1978 | Fetz et al. | 264/1.1 |
| 4,150,471 | 4/1979 | Richards et al. | 264/1.7 X |
| 4,249,271 | 2/1981 | Poler | 623/6 |
| 4,273,802 | 6/1981 | Kamada et al. | 264/1.1 X |
| 4,284,591 | 8/1981 | Neefe | 264/1.1 |
| 4,285,890 | 8/1981 | Mizutani et al. | 264/1.1 |
| 4,402,579 | 9/1983 | Poler | 623/6 X |
| 4,414,694 | 11/1983 | Choyce | 623/6 |
| 4,424,597 | 1/1984 | Schlegel | 623/6 |
| 4,615,702 | 10/1986 | Koziol et al. | 623/6 |

FOREIGN PATENT DOCUMENTS

| | | | |
|---|---|---|---|
| 1103399 | 5/1955 | France | 623/6 |
| 2081469A | 2/1982 | United Kingdom | 623/5 |
| 2114315 A | 8/1983 | United Kingdom | 623/6 |

Primary Examiner—Ronald L. Frinks
Attorney, Agent, or Firm—Frank Frisenda, Jr.

[57] ABSTRACT

The invention provides improved intraocular lens structures for surgical placement in the eye, the unique structures comprise an optical zone portion substantially centrally disposed with an integral outer haptic portion. In one embodied form, the haptic portion is composed of materials having relatively high temperature resistance such as polyimide material, and can be fabricated in a wide variety of engineered configurations. In a presently preferred embodiment, the haptic portion includes an anchoring strut in an arcuate configuration having an oblique face directed to the center of the optical zone portion. The invention further provides methods for insert molding of haptic portions to optical zone portions of the lens structures without conventional secondary operations such as drilling sites in the optic for insertion and welding of haptics. Accordingly, the unique structures and methods provide haptic portions of an infinite variety of engineered shapes which, together with the optical zone portion, are autoclavable and provide a comfortable fit for the eye. The novel lens structure combination permits a wide variety of haptic portions and optical zone portions to be conveniently assembled, thereby providing a lens structure combination which possesses appropriate haptic configuration and optical characteristics custom-fitted to a patient's individual requirements.

10 Claims, 3 Drawing Sheets

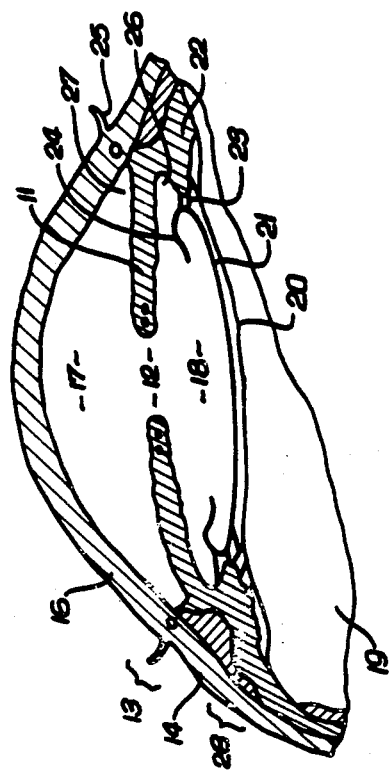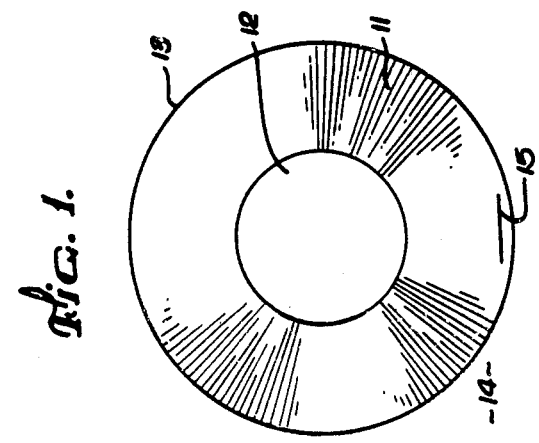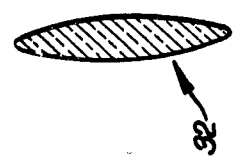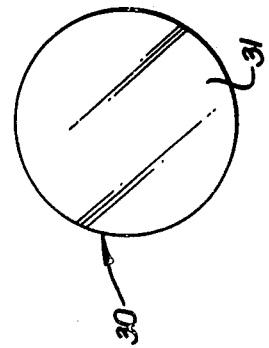

INTRAOCULAR LENS STRUCTURE WITH POLYIMIDE HAPTIC PORTION AND METHODS FOR FABRICATION

BACKGROUND OF THE INVENTION

Intraocular lenses have gained wide acceptance in replacement of human crystalline lens after a variety of cataract removal procedures. The human crystalline lens is generally recognized to be a transparent structure having a thickness of about 5 millimeters and a diameter of about 9 millimeters. The lens is suspended behind the iris by zonula fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may generally be categorized as intracapsular (in which the lens is removed together with the lens capsule) and extracapsular (in which the anterior capsule is removed with the lens, and the posterior capsule is left intact).

Since Ridley implanted the first artificial lens in about 1949, the problems associated with cataract extraction and lens implantation have received a great deal of attention from ophthalmic surgeons.

Various types of artificial lenses have been proposed, and appropriate surgical procedures have been developed which strive to reduce patient discomfort and to reduce post-operative complications. Reference is made in this connection to *Pseudophakos* by N. Jaffe, et al.; "History of Intraocular Implants" by D.P. Choyce (Annals of Ophthalomology, Oct. 1973); U.S. Pat. No. 4,251,887 issued to Anis on Feb. 24, 1981; U.S. Pat. No. 4,092,743 issued to Kelman on Nov. 8, 1977; "Comparison of Flexible Posterior Chamber Implants", presented at the American Intraocular Implant Society Symposium Apr. 23, 1982, by Charles Berkert, M.D.; and "the Simcoe Posterior Lens' (Cilco, Inc. 1980); pending U.S. Pat. Application Ser. No. 346,105, now U.S. Pat. No. 4,573,998 for "Deformable Intraocular Lens Structures and Methods and Devices for Implantation" filed Feb. 15, 1982 by the inventor Thomas R. Mazzocco, and pending U.S. Pat. Application Ser. No. 400,665 for "Improved Fixation System for Intraocular Lens Structures", filed July 22, 1982, the latter applications being commonly assigned to the instant Assignee; which disclosures are hereby incorporated by this reference.

Conventional fixation systems for positioning and for fixating the artificial lens within the eye commonly involve the use of sutures for instance, for attachment of the lens to the iris, or involve the use of supporting haptic flanges to hold the lens in position without sutures.

Kelman, in U.S. Pat. No. 4,056,855, issued Nov. 8, 1977, describes an intraocular lens and a method of its implantation through an incision in the eye in which a lens member and a supporting wire initially in disassembled condition are adapted to be introduced independently through a small incision in the eye. The supporting wire of the Kelman lens has a base portion which is adapted to fit and be mounted behind the iris of the eye, and has a pair of resilient legs projecting from the pupil, forward of the iris which are adapted to receive a lens therebetween snapped into position by resiliently parting the legs while both components are located in the eye and thereby assembling and mounting the intraocular lens in position in the anterior portion of the eye for use.

Poler in U.S. Pat. No. 4,118,808, issued Oct. 10, 1978, discloses in one embodied form, a rim of an intraocular lens having a peripheral groove and a unitary mounting adapter which is formed to permanently assemble by resilient snap action into the groove. The adapter may be formed from a single piece "blank" and may be a circumferentially continuous structure. In unstressed condition, arcs are of curvature conforming to that of the groove and are preferably at a slight radially inwardly displaced position with respect to the circle of the groove. The arcs are outwardly spread against the compliant action of loops in order to permit placement and resilient snap retention of arcs in the groove. The assembly can then be sterilized and implanted in the eye.

While the prior art intraocular lens structures of Poler and Kelman referred to above, propose to hold an optic in place by a plurality of haptics which are interlocked and built up in the eye, these surgical procedures require extreme dexterity for accurate placement of the lens structure and for constructing the assembly and present a likelihood that less skilled surgeons may knick non-repairable ocular tissue such as the iris. Moreover, should the assembled optic and haptic split, its disassembly could cause laceration of the ocular tissue or cause the optic to be displaced from its intended position.

As with any surgery, an increased number of manipulations required to fixate the lens within the eye, increases the surgical trauma to the eye. Additionally, haptic components of conventional sutureless lenses can damage ocular tissue during intra-operative lens manipulation.

Flom (U.S. Pat. No. 3,991,426) and Hartstein (U.S. Pat. No. 4,262,370), teach sutureless iris engagement fixation systems, and Anis (U.S. Pat. No. 4,251,887) and Simcoe teach sutureless fixation systems utilizing broadly curved flexible supporting loop haptics. Unfortunately, the iris engagements systems require relatively significant trauma to the iris with attendant postoperative complications. The latter known systems, while achieving fixation with little or no trauma to the iris, can still become displaced through relatively small tears in the capsular bag when they are positioned there. These tears are not uncommon, and may occur during the removal of the cataract or during the insertion of the lens.

A wide variety of haptic fixating appendages for intraocular lens structures have been developed to foster improved fixation of the optical zone portion of the lens in specific implantation techniques and for particular sizing and implantation for the surgical procedure involved. For instance, intraocular lenses have been provided conventionally with fixating appendages having compressible internal support elements; integral and non-integral fixating appendages; angulated compressible fixating appendages with internal supporting elements; compressible peripheral support rings; to name but a few species.

Similarly, a wide variety of optical zone portions for intraocular lens structures have been developed to provide proper optical characteristics, that is, diopter power of the optic, appropriate optical finish, particular sizing and the like, to provide appropriate replacement or corrective features for the human crystalline lens of the patient.

Conventional haptic designs for intraocular lens structures generally require a second operation separate and apart from the molding or other fabrication of the optical zone portion of the lens. Typically, heat staking is required to fasten the haptic portion to the optical portion of the lens. In this respect, an optical zone portion may be molded, for instance, of a hard material such as PMMA, machined in a separate operation to remove flash and to drill sites for receiving the haptic portion. One preferred material for fabricating conventional haptics is polypropylene which is typically heat set to shape the polypropylene material at a temperature of about 225 degrees farenheit, but below the plastic transition temperature of the polypropylene material. After the conventional haptic portion is heat set, it is thereafter appended to the optical zone portion such as by tack welding in which the polypropylene is fixed to the drilled site in the optical zone portion.

One disadvantage of the foregoing conventional lens structures is that polypropylene haptics can be fabricated in a limited number of configurations owing to its relatively low temperature iependence and that generally, polypropylene is fabricated in round cross section by extrusion methods.

Additionally, owing to the relatively low temperature limitation of polypropylene haptics, the assembled conventional intraocular lens structure of these materials cannot be readily autoclaved in that typical autoclaved temperatures are within a range from about 240 degrees F. to about 250 degrees F., and may require autoclaving pressures up to about 15 atmospheres. As previously mentioned, such temperature ranges and pressures would destroy the heat set configurations of the polypropylene haptic portions.

Accordingly, those skilled in the art have recognized a significant need for an improved intraocular lens structure which affords the surgeon the choice of assembling a prescribed lens combination, that is, in terms of specific optical zone portion and specific configuration for haptic portion, which are custom tailored to a patient's individual needs. Further, those skilled in the art have recognized a significant need for an improved lens structure assembly which is autoclavable and which can be conveniently manufactured to produce a lens structure with integral haptic portion minimizing the risk of optic and haptic disassembly which could cause laceration of the ocular tissue or could cause the optic to be displaced from its intended position. The present invention fulfills these needs.

SUMMARY OF THE INVENTION

This invention relates to an improved intraocular lens structure for surgical placement in the eye, the structure comprising an optical zone portion substantially centrally disposed in an outer haptic portion.

In a presently preferred embodied form, the haptic portion is composed of a material having relatively high temperature resistance sufficient to withstand typical autoclave temperature and pressures, and which can be fabricated in a wide variety of engineered configurations. Particularly suitable for such haptic portion is the polymeric material, polyimide.

The haptic portion of the inventive intraocular lens structure may be of any configuration to foster improved fixation of the optical zone portion of the lens by specific implantation techniques and for prescribed sizing and implantation for the surgical procedure involved. For instance, the haptic may be provided with fixating appendages have compressible internal support elements; integral and non-integral fixating appendages; angulated compressible fixating appendages with internal supporting elements and the like.

Similarly, a wide variety of optical zone portions may be utilized for the unique intraocular lens structure assembly in accordance with the present invention. One preferred optical zone portion is fabricated from silicone, material to provide a deformable optical zone portion. In more detail, the deformable optical zone portion of the preferred intraocular lens structure possesses memory characteristics such that the lens can be deformed by compressing, rolling, folding or stretching the optical zone portion to a diameter of 80% or less than the cross sectional diameter of the optic during insertion into the eye, yet return to its original configuration, size and fixed focal length once implanted in the eye, thereby providing a safer, more convenient and more comfortable surgical procedure. Accordingly, the preferred inventive intraocular lens structures can be implanted through smaller incisions made in the ocular tissue than would be possible with any rigid optical zone portion of comparable size.

The optical zone portion of the unique lens structure may be colored, tinted, comprise occluded portions or comprise one or more service layers thereon. Any suitable optic configuration is comprehended within the scope of the invention such as biconvex configuration, plano convex configuration, plano concave configuration, biconcave configuration, concave-convex configuration and the like.

The optical zone portion may either be relatively rigid or relatively deformable and will generally be characterized by its important parameters. In this regard, although deformable optical zone portions are preferred, relatively rigid optical zone portions such as fabricated from PMMA are also comprehended within the invention.

An important feature of the unique intraocular lens structures in accordance with the present invention, is that the haptic portion is integral with the optical zone portion of the lens. This minimizes the possibility that the optical zone portion and haptic portion will become disassembled which could cause laceration of the ocular tissue or cause the optic to be displaced from its intended position. Another important feature of the unique intraocular lens structures in accordance with the present invention, is that the haptic comprises anchoring struts of prescribed configuration which enhances stability of the intraocular lens systems.

The present invention further provides unique methods for insert molding of the optical zone portion and haptic portion of the lens structure prior to implantation within the eye.

Accordingly, the inventive methods for fabricating unique intraocular lens structures in accordance with the present invention comprises:

(a) embedding a haptic portion of engineered configuration in a removable carrier;

(b) positioning the embedded haptic portion within a mold for fabricating an optical zone portion substantially centrally disposed in relation to the haptic portion;

(c) introducing optical zone material to the mold for forming the optical zone portion of the intraocular lens structure;

(d) allowing the optical zone material to cure;

(e) removing the carrier from the haptic portion and optical zone portion assembly; and (f) removing the cured intraocular lens structure from the mold;

whereby an intraocular lens structure is provided having a haptic portion integral with an optical zone portion of the lens structure.

In a presently preferred embodiment, the engineered configuration for the haptic portion comprises anchoring haptic strut of arcuate configuration providing good resistance against tension and compression. The presently preferred removable carrier is optical wax which can be conveniently removed from the assembly by heat. Other water soluble and alcohol soluble carriers are, of course, contemplated.

After the haptic portion is embedded within the removable carrier, it may optionally be centered in a fixture and optionally cut to size, for instance, by die cutting prior to introducing optical zone material into the mold.

Curing of the optical zone material within the mold can be effected by any conventional means such as by heat, irradiation and/or by chemical agents.

Accordingly, an opthalmic surgeon may select a prescribed combination from a wide variety of haptic portions having engineered configurations and optical zone portions of prescribed optical characteristics custom fitted to a patient's individual requirements. Moreover, the haptic portion and optical zone portion may conveniently be assembled by the inventive insert molding technique to produce a stable IOL system.

The above and other objects and advantages will become apparent from the following more detailed description of the invention, taken in conjunction with the drawings.

BRIEF DESCRIPTION OF THE DRAWINGS

FIG. 1 is a stylized frontal view of a human eye illustrating a relatively small surgical incision made in the ocular tissue relative to major eye components for purposes of referencing the description of unique intraocular lens implants in accordance with the present invention;

FIG. 2 is a partially side sectional view of the human eye shown in FIG. 1 illustrating the internal condition of the ocular area after extracapsular cataract extraction in accordance with conventional procedure;

FIG. 3 is a front elevational view of one embodied form of an optical zone portion of the intraocular lens without a haptic portion to facilitate an understanding of the present invention;

FIG. 4 is a side sectional view of the optical zone portion of the intraocular lens shown in FIG. 3 of the biconvex lens specie;

FIG. 5 is a side sectional view of the optical zone portion of the intraocular lens shown in FIG. 3 of the plano convex lens specie;

FIG. 6 is a side sectional view of the optical zone portion of the intraocular lens shown in FIG. 3 of the plano concave lens specie;

FIG. 7 is a side sectional view of the optical zone portion of the intraocular lens shown in FIG. 3 of the biconcave lens specie;

FIG. 8 is a side sectional view of the optical zone portion of the intraocular lens shown in FIG. 3 of the concave-convex lens specie;

DESCRIPTION OF THE PREFERRED EMBODIMENTS

Figure 9:
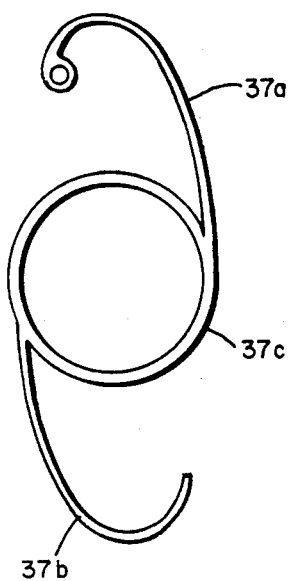
FIG. 9 is a front elevational view of one embodied form of a haptic portion without an optical zone portion to facilitate an understanding of the present invention.

The present invention provides improved intraocular lens structures for surgical placement in the eye, the structures comprising an optical zone portion substantially centrally disposed in relation to an outer haptic portion. In one embodied form, the haptic portion is composed of a polymeric material having relatively high temperature resistance such as polyimide. The haptic portion may be fabricated having a wide variety of engineered configurations and is integral with the optical zone portion of the lens structure. Accordingly, the present invention provides a new class of autoclavable and stable IOL systems which are conveniently manufactured and possess appropriate haptic configuration and optical characteristics custom fitted to a patient's individual requirements.

The present invention further provides methods for insert molding of haptic portions to the optical zone portion of the lens prior to implantation within the eye. The unique insert molding process insures uniformity of manufacturer of the inventive lenses without requiring secondary operations such as machining the optical zone portion of the lens to provide sites for appending the haptic portion of the lens thereto.

Referring now to the drawing, denoted FIG. 2, there is shown a side cross-sectional view of the eye in stylized form illustrating the major ocular components: iris 11, pupil 12, limbus 13, sclera 14, after extracapsular cataract extraction in accordance with conventional procedure.

In more detail, FIG. 2 further depicts the cornea 16 composed of clear tissue which connects the sclera 14 at the limbus 13. The anterior segment of the eye is divided into two principle chambers by the iris 11 and pupil 12. The anterior chamber 17 is defined by the space between the cornea 16 and the iris 11. The posterior chamber 18 is defined in the space between the iris 11 and the vitreous 19.

In surgical procedures commonly known as intracapsular cataract extraction, the posterior chamber 18 is bounded by the hyaloid membrane 20. In surgical procedures commonly known as the extracapsular cataract extraction, the posterior chamber 18 is bounded by the posterior capsule 21 attached to the ciliary body 22 by means of zonular fibers 23. Portions of the anterior capsule may remain as flaps 24, creating with the posterior capsule 21, the ocular portion commonly known as the "capsular bag." The posterior chamber 18 peripheral area between the iris 11 and the extension of the ciliary body 22 is referred to as the ciliary sulcus 26. The anterior chamber peripheral area between the cornea 16 and the iris 11 is referred to as the angle 27 of the eye. The area of the sclera posterior to the plane of the iris and anterior to the vitreous 19 is known as pars plana 28.

With the foregoing referenced ocular components in mind, it is a principle feature in one embodied form of the present invention to provide fixation systems for various classes of intraocular lens structures, including those lenses with deformable optical zone portions and rigid optical zone portions such that the lens may be fixated within the eye by way of surgical procedures which minimize the serious danger associated with disassembly of the haptic from the optical zone portion.

More particularly, where the improved intraocular lens structure is utilized for placement within the capsular bag, typical overall diameter of the haptic flange portion of the lens structure is from about 9 millimeters to about 12.5 millimeters. Where the haptic flange portion is sized to fit within the posterior chamber of the eye, behind the iris and in front of the ciliary processes, the typical overall diameter of the haptic flange portion would be within a range of from about 12.5 millimeters to about 14.5 millimeters. Further, where the haptic flange portion is to be utilized in placement of the intraocular lens structure within the anterior chamber of the eye, the overall diameter of the haptic flange portion will typically be from about 11 millimeters to about 14 millimeters.

It is preferable to have the haptic portion broadly curved, extending at least about 20% from the periphery of the optical zone portion of the lens. These broader curves help distribute the pressures imparted during intraocular manipulation of the lens while positioning it in place within the eye. Furthermore, such configuration provides the implanted lens with a broader contact face to resist slippage through tears or holes within the supporting ocular tissue.

As will be readily apparent by those skilled in the art, however, the foregoing typical dimensions are merely illustrative of a wide variety of suitable sizes and configurations are included within the spirit and scope of this invention.

FIG. 3 depicts one embodied form of optical zone portion 30 of an intraocular lens which is suitable for use as an artificial lens implant. In the embodied form shown, there is no haptic portion to facilitate an understanding of the invention. The optical zone portion 30 may be deformable or rigid and imparted with desirable memory characteristics, appropriate structural dimensions, and composed of an optical material such that the lens can be compatible and designed for insertion into the eye.

Preferably, a deformable optical zone portion 30 of the lens is composed of one or more materials selected from the group consisting of polyurethane elastomer, silicone elastomer, hydrogel plastic, collagen, organic or synthetic gels or combinations thereof. In one embodied form, the optical zone portion of the lens can be fabricated from one of the foregoing materials, and further comprise a thin surface layer or layers of a second or third material. Moreover, the lens may be tinted, colored or fabricated with occluded portions with selective light-absorbing components to yield transmission effects similar to a human crystalline lens.

As shown in FIGS. 4, 5, 6, 7, and 8, the optical zone portion 30 can be fabricated having a wide variety of cross-sections designed for replacement of the surgically removed human crystalline lens or for refractive correction without removal of the human crystalline lens. In this respect, the FIGS. 4–8 illustrate respectively a convex lens 32, a plano convex lens 33, a plano concave lens 34, a biconcave lens 35, and a concave-convex lens 36.

As shown in FIG. 9, the haptic portion 37 will be composed of a material having a sufficient temperature resistance for autoclaving without deleteriously affecting engineered configurations. Further, the selected material should be autoclavable to enable the assembled lens structure to be sterilized just prior to implantation.

The haptic flange portion 37 is preferably composed of a biologically compatible polymer for instance, polyimide or the like.

The selected material for the haptic portion 37 must possess suitable physical characteristics in terms of softness, compressibility, stiffness and stretchability to keep the optical zone portion 30 of the lens structure well centered and integrated with the portion 37.

In accordance with the present invention, the optical zone portion 30 of the lens structure may also be made of rigid material, such as glass or plastic suitable for optical use, for example, polymethylmethacrylate. As previously mentioned, the zone portion 30 may also be deformable in accordance with the invention described in U.S. Application Ser. No. 346,105, filed Feb. 5, 1982 by the inventor, Thomas R. Mazzocco, entitled Deformable Intraocular Lens Structures and Methods and Devices for Implantation. In this latter respect, the optical zone portion of the intraocular lens will possess memory characteristics such that the lens can be deformed by compressing, rolling, folding, or stretching the optical zone portion to a diameter of 80% or less than the cross-sectional diameter of the optic during insertion into the eye, yet return to its original configuration, size and fixed focal length once implanted in the eye. Typically, the deformable optical zone portion is fabricated from one or more suitable materials, such as polyurethane elastomer, silicone elastomer, hydrogel polymer, collagen compound, organic or synthetic gel compounds and combinations thereof.

Those skilled in the art will readily appreciate that the optical zone portion of the lens in accordance with the prevent invention, can be fabricated having a base composed of any of the foregoing materials, and further comprise a surface layer or layers of a second and third material. Moreover, the lens may be tinted, colored, or fabricated with occluded portions to yield desired transmission effects.

Additionally, the intraocular lens structures in accordance with the present invention, may comprise means for assisting manipulation, placement or fluid flow around or through the haptic flange of the lens. In this respect, the lens may be optionally provided with one or more holes, suitably located, which may extend entirely through the cross-section of the lens, or partly through the cross-section of the lens as an indentation or depression. Moreover, the haptic flange portion of the lens or optical zone portion of the lens may be made of a gas or fluid permeable material.

An important feature of the unique intraocular lens structures in accordance with the present invention, is that the haptic portion 37 is integral with the optical zone portion 30 of the lens. This minimizes the possibility of the optical zone portion 30 and the haptic portion 37 will become disassembled which could cause laceration of the ocular tissue or cause the optic to be displaced from its intended position. Another important feature of the unique intraocular lens structures in accordance with the present inventory, is that the haptic 37 possesses sufficient anchoring in the optical zone portion to provide good resistance against tension and compression during placement of the lens in the eye by the ophthalmic surgeon. In this respect, the anchoring of the haptic portion 37 within the optical zone portion 30 should be sufficient to withstand a tensile pull force of from about 50 grams pull to at least about 115 grams pulls.

Figures 13, 14:
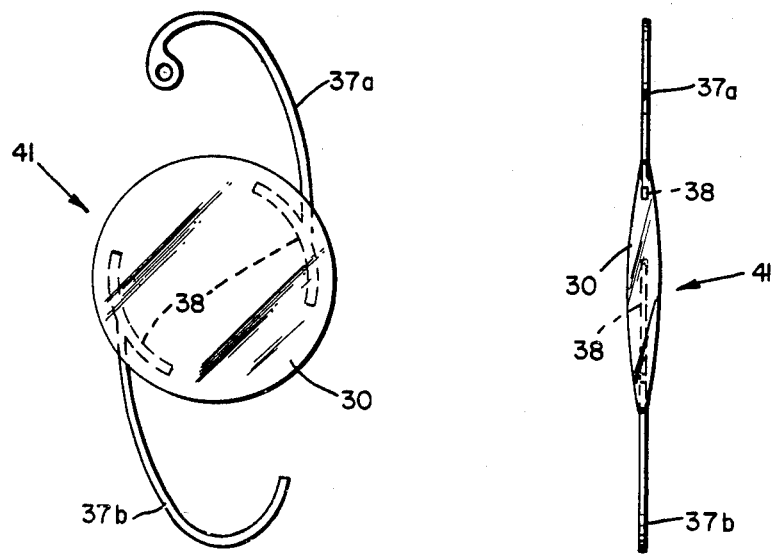
FIG. 13 is a front elevational view of one embodied form of the inventive intraocular lens structure produced in accordance with the present invention.
FIG. 14 is a side sectional view of the inventive intraocular lens structure depicted in FIG. 13 in accordance with the present invention.

In one particular preferred embodiment, the haptic flange portion 37 as shown in FIG. 13 is configured with one or more anchoring struts 38. Preferably, two anchoring struts are integral with the optical zone zone portion 30 and insert molded at substantially opposite locations with respect to each other in the peripheral section of the optical zone portion 30. The preferred anchoring struts 38 may generally be described as having arcuate configurations including an oblique face directed to the center of the optical zone portion 30.

In one presently preferred embodied form, the anchoring struts 38 include arcuate members of about 80 degrees each along the 360 degree peripheral section of a generally circular optical zone portion such as depicted in FIG. 13. In the depicted embodied form, each anchoring strut 38 is of about 0.135 inches in length.

The haptic portion 37 should, of course, meet the industry standard for instance American National Standard Institute (ANSI) Z-AD.

In a presently preferred intraocular lens structure, the optical zone portion is fabricated from an autoclavable silicone material, particularly, peroxide catalyzed or platinum catalyzed medical grade silicone. The silicone material may be fabricated from silica filler such as RMZ-1. In the preferred embodied form, the haptic portion 37 is an etched polyimide loop which can be etched by conventional process such as photo etching. Typically, the polyimide material will maintain its stability over a temperature range of up to 700 to 800 degrees Fahrenheit.

The present inventory further provides unique methods for insert molding of the optical zone portion 30 and haptic portion 37 of the lens structure prior to implantation within the eye.

Accordingly, the inventive methods for fabricating unique intraocular lens structures in accordance with the present inventory comprises:

(a) embedding a haptic portion of engineered configuration in a removal carrier;

(b) positioning the embedded haptic portion within a mold for fabricating an optical zone portion substantially centrally disposed in relation to the haptic portion;

(c) introducing optical zone material to the mold for forming the optical zone portion of the intraocular lens structures;

(d) allowing the optical zone material to cure;

(e) removing the carrier from the haptic portion and the optical zone portion assembly; and (f) removing the cured intraocular lens structure from the mold;

whereby by an intraocular lens structure is provided having an haptic portion integral with an optical zone portion of the lens structure.

Figure 10:
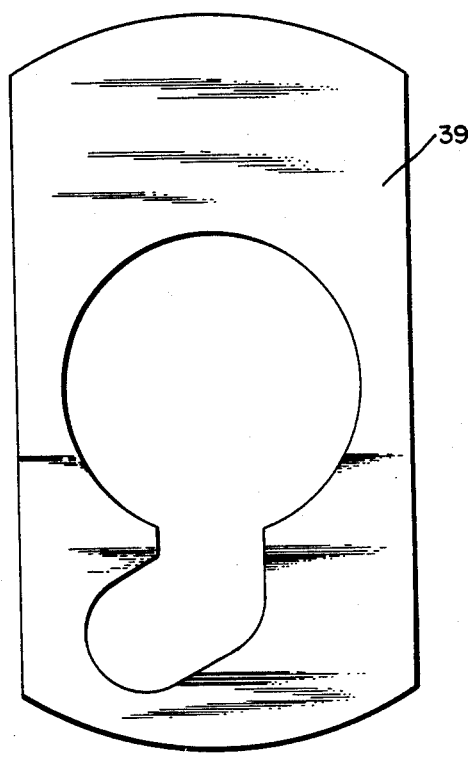
FIG. 10 is a front elevational view of a die member for cutting the haptic portion shown in FIG. 9 once embedded in a removable carrier.

Referring to FIG. 9, one embodied form of haptic portion 37 is depicted without an optical zone portion 30 to facilitate an understanding of the present inventory. Illustrated in FIG. 10 is front view of a suitable die member 39 for cutting the haptic portion 37 once embedded in a removal carrier 40.

Figure 11:
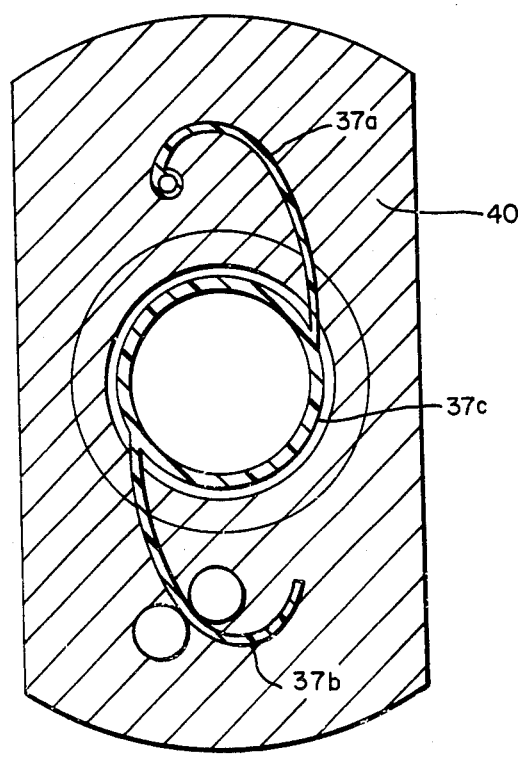
FIG. 11 is a front elevational view of the haptic portion shown in FIG. 9 embedded in a removable carrier for maintaining the prescribed position of the haptic portion prior to and during introduction of material into a mold for forming the optical zone portion of the lens structure.

As seen most clearly in FIG. 11, the haptic portion 37 shown in FIG. 9 is embedded in a removal carrier 40 for maintaining the prescribed position of the haptic portion 37 prior to and during introduction of material into a mold for forming the optical zone portion 30 of the lens structure.

Figure 12:
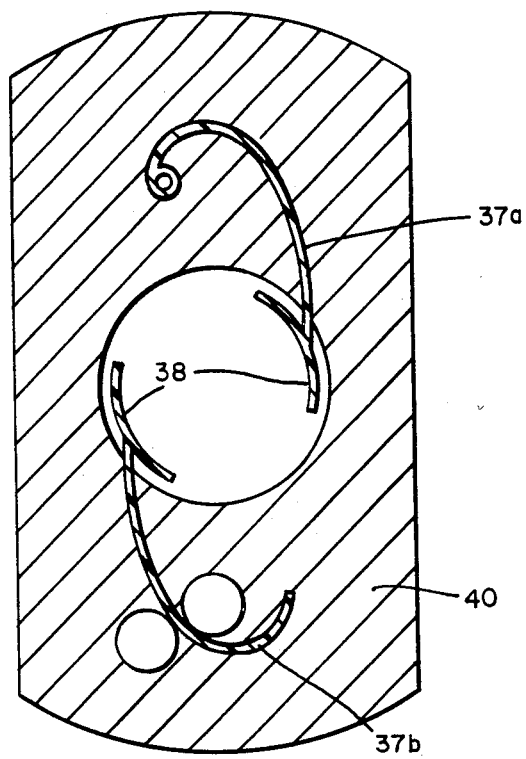
FIG. 12 is a front elevational view of the embedded haptic portion of the intraocular lens after a central section of haptic has been die cut.

As shown in FIG. 12, the embedded haptic portion 37 of the intraocular lens is depicted. After a central section of the haptic 37 has been cut with the die member 39. Of course, those skilled in the art will appreciate that a centering fixture may be utilized for receiving the removable carrier embedded with the haptic portion 37 during the cutting procedure.

The resultant intraocular lens structure 41 in accordance with the present invention is depicted in FIGS. 13 and 14.

The presently preferred removable carrier is optical wax which can be conveniently removed from the mold assembly by heat. Other water soluble and alcohol soluble carriers are, of course, contemplated within the spirit and scope of the invention.

As previously mentioned, after the haptic portion 37 is embedded within the removable carrier to, it may optionally be centered in a fixuate (not shown) and optionally cut to size, for instance, by the illustrated die cutting mechanism prior to introducing optical zone material into the mold.

Curing of the optical zone material within the mold can be effected by any conventional means such as by heat, irradiation and/or by chemical agents. Typically, a conventional silicone cure cycle will involve a curing time of from about 15 minutes to about one hour and temperature within a range of about 150 degrees C.

If heat is used to dissolve the removable carrier, those skilled in the art will readily appreciate that the mold for the optical zone portion may include a shoulder to receive the melted or dissolved wax in a location which will not interfere with the mold cavity for the optical zone 30.

Accordingly, the inventive methods provide for insert molding of haptics to optical zone portions and provide lens structure combination which possess appropriate haptic configuration and optical characteristics custom-fitted to a patient's individual requirements.

Typically, the inventive intraocular lens structures in accordance with the present invention will have a total length from about 9 millimeters to about 14 millimeters, and a width from about 4 millimeters to about 14 millimeters, and can be fabricated having a wide range of index of refraction. The optical zone portions will typically have a thickness of from about 0.1 millimeters to about 1.0 millimeters and a diameter in the range of from about 4 millimeters to about 6 millimeters.

It will be apparent from the foregoing that, while particular forms of the invention have been illustrated and described, various modifications can be made without departing from the spirit and scope of the invention. Accordingly, it is not intended that the invention be limited except as by the intended claims.

We claim:

1. A method for fabricating intraocular lens structure by inserting holding technique, the structure including a haptic portion and an optical zone portion, the method comprising the steps of:
   (a) embedding a haptic portion of engineered configuration in a removable carrier;
   (b) positioning said imbedded haptic portion with a mold for fabricating an optical zone portion substantially centrally disposed in relation to said haptic portion;
   (c) introducing optical zone material to said mold for forming said optical zone portion of said intraocular lens structure;
   (d) allowing said optical zone material to cure;
   (e) removing said carrier from said haptic portion and optical zone portion assembly; and
   (f) removing the cured intraocular lens structure from said mold;
   whereby an intraocular lens structure is provided having a haptic portion integral with an optical zone portion of the lens structure.

2. The method for fabricating intraocular lens as defined in claim 1 wherein said removal carrier is optical wax.

3. The improved method for fabricating intraocular lens as defined in claim 1 wherein said carrier is removal by heat.

4. The improved method for fabricating intraocular lens structures as defined in claim 1 wherein said carrier is soluble in water.

5. The improved method for fabricating intraocular lens structures as defined in claim 1 wherein said carrier is soluble in alcohol.

6. The improved method for fabricating intraocular lens as defined in claim 1 and further comprising the step of die cutting said haptic portion after embedment in said removal carrier.

7. The improved method for fabricating intraocular lens as defined in claim 1 and further comprising the step of centering said embedded haptic portion within a fixture and thereafter cutting said haptic portion by means of a die.

8. The improved method for fabricating intraocular lens as defined in claim 1 wherein said step of curing said optical zone material is effected by heat.

9. The improved method for fabricating intraocular lens as defined in claim 1 wherein said step of curing said optical zone material is effected by irradiation.

10. The improved method for fabricating intraocular lens as defined in claim 1 wherein said step of curing said optical zone material is effected by chemical agents.

* * * * *